US006703349B2

(12) United States Patent
Silverman et al.

(10) Patent No.: US 6,703,349 B2
(45) Date of Patent: Mar. 9, 2004

(54) ENHANCED HERBICIDE COMPOSITION

(75) Inventors: F. Paul Silverman, Highland Park, IL (US); Peter D. Petracek, Grayslake, IL (US); Daniel F. Heiman, Libertyville, IL (US); Prem Warrior, Green Oaks, IL (US)

(73) Assignee: Valent BioSciences Corporation, Libertyville, IL (US)

( * ) Notice: Subject to any disclaimer, the term of this patent is extended or adjusted under 35 U.S.C. 154(b) by 0 days.

(21) Appl. No.: 10/304,808

(22) Filed: Nov. 26, 2002

(65) Prior Publication Data

US 2003/0114310 A1 Jun. 19, 2003

Related U.S. Application Data

(60) Provisional application No. 60/333,571, filed on Nov. 27, 2001.

(51) Int. Cl.$^7$ ................................................ A01N 43/36
(52) U.S. Cl. ........................................ 504/286; 504/318
(58) Field of Search .................................. 504/286, 318

(56) References Cited

U.S. PATENT DOCUMENTS

| 4,931,581 A | | 6/1990 | Schurter et al. |
|---|---|---|---|
| 5,015,649 A | | 5/1991 | Kunz |
| 5,767,373 A | * | 6/1998 | Ward et al. |
| 5,939,602 A | * | 8/1999 | Volrath et al. |
| 6,018,105 A | * | 1/2000 | Johnson et al. |
| 6,218,336 B1 | | 4/2001 | Coleman |
| 2002/0004457 A1 | | 1/2002 | Nevill et al. |

OTHER PUBLICATIONS

O.C. Knorzer et al, Peroxidizing Herbicides, (1999) pp. 302–327.
M.V. Rao et al., Plant Physiol (1997) 115:137–149.
N.E. Strobel et al., Phytopathology (1995) pp. 1306–1310.
L. Klepper, Pesticide Biochemistry and Physiology, 32, 173–179 (1988).
E.A. Ananieva et al., J. Plant Physiol, 159, 685–693 (2002).
European Commision, 17$^{th}$ International Conference on Plant Growth Substances, Brno, Czech Republic Jul. 1–6, 2001.

* cited by examiner

*Primary Examiner*—Sabiha Qazi
(74) *Attorney, Agent, or Firm*—Wood, Phillips, Katz, Clark & Mortimer

(57) ABSTRACT

A herbicidal composition comprising a protoporphyrinogen oxidase inhibitor and a salicylate or another SAR inducer or a combination thereof and methods of controlling plant growth with said composition are disclosed.

16 Claims, No Drawings

ENHANCED HERBICIDE COMPOSITION

This application claims the benefit of provisional application Ser. No. 60/333,571, filed on Nov. 27, 2001.

BACKGROUND OF THE INVENTION

A variety of herbicides have been used to kill unwanted plants (weeds) in crop fields or orchards. Typically, these herbicides are sprayed on the soil (preemergence) or on the plants (postemergence).

Herbicides are expensive, and their use may result in unintentional consequences such as groundwater contamination, environmental damage, herbicide-resistant weeds, and human and mammalian health concerns.

There are many classes of herbicides which may be grouped based on their mode of action. One class of herbicides of particular interest is the protoporphyrinogen oxidase (PPO) inhibitors, which act by inhibiting the synthesis of chlorophyll in the plastids of plants. Inhibition of this enzyme results in the generation of active oxygen species, which disrupt cell membranes and kill the plant.

It is an object of the present invention to reduce the amount of herbicide required for effective treatment.

SUMMARY OF THE INVENTION

The present invention is directed to a composition comprising a PPO inhibitor and salicylate or another systemic acquired resistance (SAR) inducer, or a combination thereof.

As used herein, "salicylate" is defined as any substituted or unsubstituted benzoic acid having a hydroxyl group in the 2- or ortho-position, or a biologically acceptable salt or biological or chemical precursor thereof. Substitution on the benzoic acid includes mono- di-, tri- or tetra-substitution in the 3-, 4-, 5- and/or 6-positions: substituents may be chosen in any combination from: lower alkyl groups of 1 to 4 carbons; an alkyl bridge containing 3 or 4 carbons attached to the benzoic acid at two adjacent points; lower alkoxy groups of from 1 to 4 carbons; the halogens fluorine, chlorine, bromine or iodine; an amino group, wherein the nitrogen may carry 0, 1, or 2 identical or different lower alkyl groups of from 1 to 4 carbons each; the nitro group; the formyl group; the acetyl group; the hydroxymethyl group; the methoxycarbonyl group; the carboxamido or sulfonamido groups wherein the nitrogen may carry 0, 1 or 2 identical or different lower alkyl substituents of from 1 to 4 carbons each; the cyano group; an alkylthio-, alkylsulfoxy- or alkylsulfonyl group, wherein the alkyl group is comprised of from 1 to 4 carbons; or a mono-, di- or trifluoromethyl group. Biologically acceptable salts include those of the common alkali metals sodium and potassium, the alkaline earths magnesium or calcium, zinc, or ammonium or simple alkylammonium cations such as mono-, di-, tri- or tetramethylammonium or other ammonium cations bearing up to 7 carbons. Biological or chemical precursors of 2-hydroxylated benzoic acid include non-hydroxylated benzoic acid and derivatives thereof having at least one ortho-position free, wherein the hydroxyl group is introduced biologically by the natural metabolic processes of the plant to which it is applied. Biological or chemical precursors of 2-hydroxylated benzoic acid also include benzoic acid compounds wherein the hydroxyl group in the 2-position is masked chemically in such a way that the masking group is labile and is easily removed once the compound has been applied to a plant, either by an enzymatic process of the plant's normal metabolism or by slow spontaneous hydrolysis. Examples of such masking groups include esters with monocarboxylic acids of from 1 to 7 carbons and trialkylsilyl ethers containing from 3 to 13 carbons. Furthermore, the term "salicylate" as used herein is understood to include mixtures of two or more of the individual pure substances defined above.

A systemic acquired resistance (SAR) inducer is defined as any compound which has the ability to turn on resistance in a plant to a disease-causing agent, which include, but are not limited to a virus, a bacterium, a fungus, or combinations of these agents. In addition, an SAR inducer may induce resistance to insect feeding in a plant, as described by Enyedi et al. (1992; Cell 70: 879–886). Exemplary SAR inducers cover many structural families of compounds, but are united by their ability to induce a resistance to plant diseases and pest feeding.

The present invention is also directed to a method of enhancing the herbicidal activity of a PPO inhibitor comprising adding to said PPO inhibitor an effective amount of salicylate or another SAR inducer, or a combination thereof.

The present invention is also directed to a method of controlling plant growth comprising applying to a plant a herbicidally effective amount of a herbicidal composition comprising a PPO inhibitor and salicylate or another SAR inducer or a combination thereof.

Yet another aspect of this invention is directed to the safening activity of salicylate or another SAR inducer or a combination thereof against herbicide damage on crops.

DETAILED DESCRIPTION OF THE INVENTION

The compositions of the present invention contains from 99.999% to 0.001% PPO inhibitor and from 99.999% to 0.001% salicylate or another SAR inducer or a combination thereof, preferably from 99.99% to 0.005% PPO inhibitor and from 99.99% to 0.005% salicylate or another SAR inducer or a combination thereof and most preferably from 99.9% to 0.001% PPO inhibitor and from 99.9% to 0.01% salicylate or another SAR inducer or a combination thereof. In addition to the PPO inhibitor and salicylate or another SAR inducer, the compositions of the present invention may contain inert solids or liquids such as water or organic solvents.

The compositions of the present invention may also be formulated as an aqueous herbicidal concentrate which is sufficiently storage stable for commercial use and which is diluted with water before use. Such concentrates have a concentration of from 100% to 0.01% of the herbicidal compositions of the present invention, preferably 50% to 0.1% and most preferably 30% to 1%.

The compositions of the present invention are dispersed or dissolved in water to a concentration of from 15% to 0.0015%, preferably 5.0% to 0.002% and most preferably 0.6% to 0.05% for application.

In an alternative embodiment of the present invention, the PPO inhibitor may be formulated as a concentrate and salicylate or another SAR inducer or a combination thereof may be formulated as a concentrate. The two concentrates are then mixed and diluted prior to use.

Suitable PPO inhibitors include diphenylethers such as arifluorfen marketed as Blazer®, fomesafen marketed as Flexstar® and Reflex®, lactofen marketed as Cobra® and flumioxazin marketed as Valor®; N-phenylphthalimides such as flumiclorac marketed as Resource® and aryl triazones such as sulfentrazone marketed as Authority® and carfentrazone marketed as Aim®.

The herbicide synergists useful in the present invention include salicylate and SAR inducers such as Actigard™ (Acibenzolar-S-methyl; 1,2,3-benzothiadiazole-7-carbothioic acid S-methyl ester; CAS Registry No. 135158-54-2), sold by Syngenta Crop Protection, Greensboro, N.C. Compositions of the present invention include both solid and liquid compositions, which are ready for immediate use, and concentrated compositions, which require dilution before use, usually with water.

The solid compositions may be in the form of granules, or dusting powders wherein the active ingredient is mixed with a finely divided solid diluent (e.g. kaolin, bentonite, kieselguhr, dolomite, calcium carbonate, talc, powdered magnesia, Fuller's earth and gypsum). They may also be in the form of dispersible powders or grains, comprising a wetting agent to facilitate the dispersion of the powder or grains in liquid. Solid compositions in the form of a powder may be applied as foliar dusts.

Liquid compositions may comprise a solution, suspension or dispersion of the active ingredients in water optionally containing a surface-active agent, or may comprise a solution or dispersion of the active ingredient in a water immiscible organic solvent which is dispersed as droplets in water. Preferred active ingredients of the composition of the present invention are water-soluble herbicides or are readily suspended in water and it is preferred to use aqueous compositions and concentrates.

The composition of the present invention may contain additional surface active agents, including for example surface active agents to increase the compatibility or stability of concentrated compositions as discussed above. Such surface-active agents may be of the cationic, anionic, or non-ionic or amphoteric type or mixtures thereof. The cationic agents are, for example, quaternary ammonium compounds (e.g. cetyltrimethylammonium bromide). Suitable anionic agents are soaps, salts of aliphatic mono esters of sulphuric acid, for example sodium lauryl sulphate; and salts of sulphonated aromatic compounds, for example sodium dodecylbenzenesulphonate, sodium, calcium, and ammonium lignosulphonate, butylnaphthalene sulphonate and a mixture of the sodium salts of diisopropyl and triisopropylnaphthalenesulphonic acid. Suitable non-ionic agents are the condensation products of ethylene oxide with fatty alcohols such as oleyl alcohol and cetyl alcohol, or with alkylphenols such as octyl- or nonyl-phenol or octylcresol. Other non-ionic agents are the partial esters derived from long chain fatty acids and hexitol anhydrides, for example sorbitan monolaurate; the condensation products of the partial ester with ethylene oxide; the lecithins; and silicone surface active agents (water soluble or disperible surface active agents having a skeleton which comprises a siloxane chain e.g. Silwet L77®). A suitable mixture in mineral oil is ATPLUS 411 F®.

Other adjuvants commonly utilized in agricultural compositions include compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be formulated with liquid fertilizers or solid, particulate fertilizer carriers such as ammonium nitrate, urea, and the like.

The rate of application of the composition of the present invention will depend on a number of factors including, for example, the active ingredients, the plant species whose growth is to be inhibited, the formulation and the method of application, as for example, spraying, addition to irrigation water or other conventional means. As a general guide, however, the application rate is from 5.0% to 0.01%, preferably from 1.0% to 0.01%(v/v) in the spray mixture. The composition of the present invention may be used for preemergence and postemergence control of susceptible weeds.

Representative plant species that may be treated with the composition of the present invention include *Nicotiana tabacum* (tobacco), *Glycine max* (soybean), *Setaria faberi* (giant foxtail), *Convolvulus arvenis* (morning glory), *Xanthrum strumarium* (cocklebur), *Chenopodium album* (lambsquarter), *Amaranthus retroflexus* (red root pigweed), and *Amaranthus rudis* (water hemp).

The present invention may be illustrated by the following representative examples:

EXAMPLE 1

Ultra pure water was used in preparing solutions. For active ingredients (e.g. lactofen or flumioxazin), the active ingredient was dissolved in a small amount of solvent (dimethyl sulfoxide (DMSO) or 1-methyl-2-pyrrolidone), and then water was added. Spray solutions were used as soon as possible after mixing.

The herbicides and spray adjuvants used in these studies included: Cobra 2 EC (emulsifiable concentrate; 2 lbs lactofen per gallon; 239 g/L), crop oil concentrate (COC; Orchex 796, 83%; Ag Plus300f, 17%), flumioxazin, lactofen, Phoenix (emulsifiable concentrate; 2 lbs lactofen per gallon; 239 g/L), salicylic acid (SA), sodium salicylate (NaSA) or Actigard™ 50WG (50% Acibenzolar-S-methyl).

In all herbicide applications, plants were sprayed with a sufficient volume to insure good coverage, which resulted in runoff of the spray solution. COC was added to all spray solutions at a rate of 0.25% (v/v). COC in water was used as the control.

After spraying, plants were allowed to dry at room temperature (about 25° C.). They were then moved to the greenhouse, and plants were arranged in a randomized complete block experimental design. Plants were evaluated for phytotoxicity/herbicidal effects at 24 hours and 7 to 9 days after spraying, assessing damage according to the following scale:

1=No damage
2=25% leaf area affected
3=50% leaf area affected
4=75% leaf area affected
5=100% leaf area affected Plants were rated for re-growth at 7 to 9 days after treatment according to the following scale:

1=Healthy new growth
2=75% of control regrowth
3=50% of control regrowth
4=25% of control regrowth
5=No new growth All the data were subject to an analysis of variance, and the mean separations were determined with Duncan's multiple range test at $p=0.05$.

The addition of salicylate synergized Cobra® activity on tobacco and lambsquarter, but not on soybean, waterhemp, giant foxtail, or cocklebur (Table 1). The effect of salicylate was greatest when measured at 24 hours after herbicide application, but in some cases persisted to the second evaluation at 8 days after application, showing that the addition of salicylate increased the rate of weed kill as well as the magnitude of herbicide damage.

TABLE 1

The effect of salicylate on herbicidal activity of Cobra.

| Plant | Treatment | 24 hour phytotoxicity Rating (1 = least damage, 5 = most) | 8 day phytotoxicity Rating (1 = least damage, 5 = most) | 8 day new growth rating (1 = healthy new growth, 5 = no new growth) |
|---|---|---|---|---|
| Tobacco | Control | 1.5 a | 2.0 b | 1.0 a |
| | NaSA (1.6 g/L) | 1.7 a | 1.0 a | 1.0 a |
| | Cobra (0.124 mL/L) | 3.5 b | 3.8 c | 4.7 b |
| | Cobra (0.124 mL/L) + NaSA (1.6 g/L) | 4.5 c | 4.5 d | 4.3 b |
| Lambs-quarter | Control | 1.0 a | 1.0 a | 1.0 a |
| | NaSA (1.6 g/L) | 1.8 a | 1.0 a | 1.0 a |
| | Cobra (0.124 mL/L) | 3.0 b | 4.5 b | 4.0 b |
| | Cobra (0.124 mL/L) + NaSA (1.6 g/L) | 4.2 c | 5.0 b | 5.0 b |
| Soybean | Control | 1.0 a | 1.0 a | 1.0 a |
| | NaSA (1.6 g/L) | 1.2 a | 1.7 a | 1.2 a |
| | Cobra (0.124 mL/L) | 3.6 c | 3.7 b | 3.0 b |
| | Cobra (0.124 mL/L) + NaSA (1.6 g/L) | 2.9 b | 3.8 b | 2.8 b |
| Waterhemp | Control | 1.0 a | 1.0 a | 1.0 a |
| | NaSA (1.6 g/L) | 1.0 a | 1.5 a | 1.0 a |
| | Cobra (0.124 mL/L) | 5.0 b | 5.0 b | 5.0 b |
| | Cobra (0.124 mL/L) + NaSA (1.6 g/L) | 4.8 b | 5.0 b | 5.0 b |
| Giant Foxtail | Control | 1.0 a | 1.0 a | 1.0 a |
| | NaSA (1.6 g/L) | 1.0 a | 1.0 a | 1.0 a |
| | Cobra (0.124 mL/L) | 4.0 b | 3.0 b | 2.8 b |
| | Cobra (0.124 mL/L) + NaSA (1.6 g/L) | 4.0 b | 3.0 b | 2.8 b |
| Cocklebur | Control | 1.0 a | 1.0 a | 1.0 a |
| | NaSA (1.6 g/L) | 1.0 a | 1.0 a | 1.0 a |
| | Cobra (0.124 mL/L) | 5.0 c | 5.0 b | 5.0 b |
| | Cobra (0.124 mL/L) + NaSA (1.6 g/L) | 4.2 b | 5.0 b | 5.0 b |

In Table 2, the effect of salicylate on the herbicidal effect of Cobra® and its active ingredient, lactofen, is presented. The ability of salicylate to increase lactofen activity on tobacco demonstrates that the salicylate/Cobra® effect is not due to a formulation component. On soybeans, salicylate did not affect lactofen-induced phytotoxicity.

TABLE 2

The effect of salicylate on herbicidal activity of Cobra and lactofen.

| Plant | Treatment | 24 hour phytotoxicity Rating (1 = least damage, 5 = most) | 8 day phytotoxicity Rating (1 = least damage, 5 = most) | 8 day new growth rating (1 = healthy new growth, 5 = no new growth) |
|---|---|---|---|---|
| Tobacco | Control | 1.0 a | 1.0 a | 1.0 a |
| | NaSA (1.6 g/L) | 2.2 a | 2.2 b | 1.2 a |
| | NaSA (8.0 g/L) | 4.4 d | 4.5 cd | 4.5 b |
| | Cobra (0.124 mL/L) | 2.6 bc | 2.9 b | 4.4 b |
| | Cobra (0.124 mL/L) + NaSA (1.6 g/L) | 4.6 d | 5.0 d | 5.0 b |
| | Lactofen (0.030 g/L) | 3.1 c | 4.2 c | 5.0 b |
| | Lactofen (0.030 g/L) + NaSA (1.6 g/L) | 4.4 d | 4.8 cd | 4.9 b |
| Soybean | Control | 1.0 a | 1.0 a | 1.0 a |
| | NaSA (1.6 g/L) | 1.4 a | 1.7 b | 2.0 b |
| | NaSA (8.0 g/L) | 3.2 c | 3.9 d | 4.2 d |
| | Cobra (0.124 mL/L) | 2.1 b | 2.6 c | 2.5 bc |
| | Cobra (0.124 mL/L) + NaSA (1.6 g/L) | 2.4 b | 2.7 c | 3.2 cd |
| | Lactofen (0.030 g/L) | 2.4 b | 2.7 c | 2.6 bc |
| | Lactofen (0.030 g/L) + NaSA (1.6 g/L) | 2.5 b | 2.7 c | 2.3 bc |

The ability of salicylates to safen crop plants against herbicide damage has also been observed. This effect may be seen in all plants grown for their commercial value including, but not limited to agronomic, floricultural, horticultural and tree fruit and vegetable crops. Specifically, this includes agronomic plants, such as soybean and rice. In soybean, the ability of salicylate was observed to decrease and delay herbicide-induced damage (Table 1). This action can provide the plant with both increased health and re-growth (Table 2). By decreasing the yield drag due to herbicide damage, salicylate application may increase yields in production programs where herbicides are used. This may be important where disease pressure is severe, and PPO inhibiting herbicides are used for plant protection.

In Table 3, the effect of salicylate on the herbicidal effect of Cobra and its active ingredient, lactofen, on morning glory is presented. This date shows that salicylate increases the herbicidal activity of both lactofen and its formulated product Cobra®.

TABLE 3

Effect of salicylate on herbicidal activity of Cobra and lactofen.

| Plant | Treatment | 24 hour phytotoxicity Rating (1 = least damage, 5 = most) |
|---|---|---|
| Morning glory | NaSA (1.6 g/L) | 1.7 a |
| | Cobra (0.124 mL/L) | 3.0 b |
| | Cobra (0.124 mL/L) + NaSA (1.6 g/L) | 3.7 cd |
| | Lactofen (0.030 g/L) | 3.3 bc |
| | Lactofen (0.030 g/L) + NaSA 1.6 g/L) | 4.0 d |

In Table 4, the effects of salicylate on the herbicidal effect of Cobra® and the PPO inhibitor compound, flumioxazin, are presented. The ability of salicylate to increase flumioxazin activity on tobacco demonstrates that the salicylate effect on Cobra®/lactofen may be a generalized phenomenon among PPO inhibitors. On pigweed, salicylate increased both the Cobra and flumioxazin herbicidal activity. However, the effect was not statistically significant.

TABLE 4

Effect of salicylate on herbicidal activity of Cobra and flumioxazin.

| Plant | Treatment | 24 hour phytotoxicity Rating (1 = least damage, 5 = most) | 9 day phytotoxicity Rating (1 = least damage, 5 = most) |
|---|---|---|---|
| Tobacco | Control | 1.0 a | 1.0 a |
|  | NaSA (1.6 g/L) | 1.5 a | 1.5 b |
|  | Cobra (0.124 mL/L) | 2.9 b | 4.7 c |
|  | Cobra (0.124 mL/L) + NaSA (1.6 g/L) | 3.6 c | 4.8 cd |
|  | Flumioxazin (0.015 g/L) | 3.7 c | 5.0 d |
|  | Flumioxazin (0.015 g/L) + NaSA (1.6 g/L) | 4.6 d | 5.0 d |
| Pigweed | Control | 1.0 a | 1.0 a |
|  | NaSA (1.6 g/L) | 1.9 a | 1.1 a |
|  | Cobra (0.124 mL/L) | 3.4 b | 5.0 b |
|  | Cobra (0.124 mL/L) + NaSA (1.6 g/L) | 4.1 bc | 5.0 b |
|  | Flumioxazin (0.015 g/L) | 4.2 bc | 5.0 b |
|  | Flumioxazin (0.015 g/L) + NaSA (1.6 g/L) | 4.6 c | 5.0 b |

Salicylates have been reported to induce plant resistance to pathogen attack (Raskin, 1992) and so it is reasonable to expect that other inducers of the plant defense response may also synergize PPO inhibiting herbicides. Other systemic acquired resistance inducers including Actigard may act as synergists. The results shown in Table 5 demonstrate the ability of Actigard to synergize Cobra® treatment of tobacco.

TABLE 5

Effect of salicylate or Actigard on herbicidal activity of Cobra.

| Plant | Treatment | 24 hour phytotoxicity rating (1 = least damage, 5 = most) | 8 d phytotoxicity rating (1 = least damage, 5 = most) |
|---|---|---|---|
| Tobacco | Control | 1 | 1 |
|  | NaSA (1.6 g/L) | 2 | 2 |
|  | Actigard (0.19 g/L) | 1 | 1 |
|  | Cobra (0.124 mL/L) | 3 | 3 |
|  | Cobra (0.124 mL/L) + NaSA (1.6 g/L) | 4 | 5 |
|  | Cobra 0.124 mL/L + Actigard (0.19 g/L) | 3 | 4 |

The addition of salicylate increased Phoenix® (lactofen) herbicidal activity on Burley tobacco in the field (Table 6). The effect was apparent 1 day after herbicide application and persisted throughout until day 7 of the experiment.

TABLE 6

Effect of salicylate on Phoenix herbicidal activity on Burley tobacco.

| Treatment | Phytotoxicity at 1 day: percent leaf area affected | Phytotoxicity at 3 days: percent leaf area affected | Phytotoxicity at 7 days: percent leaf area affected | Phytotoxicity at 14 days: percent leaf area affected |
|---|---|---|---|---|
| Control | 0.8 a | 3 a | 2.8 a | 2.5 a |
| NaSA 1.6 g/L | 1.3 a | 2.8 a | 3 a | 4.8 a |
| Phoenix 0.54 mL/L | 4.8 b | 15.8 b | 25 b | 18.8 b |
| Phoenix 0.54 mL/L + NaSA 1.6 g/L | 22.5 c | 35.8 c | 33 c | 28.8 b |

What is claimed is:

1. A herbicide composition comprising a protoporphyrinogen oxidase inhibitor and salicylate or another SAR inducer or a combination thereof.

2. The herbicide composition of claim 1 wherein the protoporphyrinogen oxidase inhibitor is lactofen.

3. The herbicide composition of claim 1 wherein the protoporphyrinogen oxidase inhibitor is flumioxazin.

4. The herbicide composition of claim 1 wherein the protoporphyrinogen oxidase inhibitor comprises from 99.99% to 0.001% of the composition and the salicylate or other SAR inducer comprises from 99.99% to 0.001% of the composition.

5. The herbicide composition of claim 1 that is suspended, dispersed or dissolved in water.

6. The herbicide composition of claim 5 wherein the water comprises from 0.1% to 99.9% of the composition.

7. The herbicide composition of claim 1 comprising a protoporphyrinogen oxidase inhibitor and salicylate.

8. The herbicide composition of claim 7 wherein the salicylate is salicylic acid or a biologically acceptable salt thereof.

9. The herbicide composition of claim 7 wherein the salicylate is sodium salicylate.

10. The herbicide composition of claim 1 comprising a protoporphyrinogen oxidase inhibitor and a SAR inducer.

11. The herbicide composition of claim 10 wherein the SAR inducer is 1,2,3-benzothiodiazole-7-carbothioic acid S-methyl ester.

12. A method enhancing the herbicidal activity of a protoporphyrinogen oxidase inhibitor comprising adding to said inhibitor an effective amount of salicylate or another SAR inducer or a combination thereof.

13. A method of controlling plant growth comprising applying to a plant a herbicidally effective amount of a herbicidal composition of claim 1.

14. A herbicide composition comprising a protoporphyrinogen oxidase inhibitor and a salicylate.

15. A method of controlling plan growth comprising applying to a plant a herbicidally effective amount of a herbicidal composition of claim 14.

16. The method of claim 12 wherein a salicylate is added to the protoporphyrinogen oxidase inhibitor.

* * * * *